(12) United States Patent
Colborn

(10) Patent No.: US 8,874,229 B2
(45) Date of Patent: Oct. 28, 2014

(54) DELIVERING SCHEDULED AND UNSCHEDULED THERAPY WITHOUT DETRIMENT TO BATTERY LIFE OR ACCURACY OF LONGEVITY PREDICTIONS

(75) Inventor: John C. Colborn, League City, TX (US)

(73) Assignee: Cyberonics, Inc., Houston, TX (US)

( * ) Notice: Subject to any disclaimer, the term of this patent is extended or adjusted under 35 U.S.C. 154(b) by 634 days.

(21) Appl. No.: 12/769,134

(22) Filed: Apr. 28, 2010

(65) Prior Publication Data

US 2011/0270359 A1 Nov. 3, 2011

(51) Int. Cl.
| A61N 1/00 | (2006.01) |
| A61N 1/02 | (2006.01) |
| A61N 1/36 | (2006.01) |
| A61N 1/378 | (2006.01) |
| A61N 1/08 | (2006.01) |

(52) U.S. Cl.
CPC ............ *A61N 1/36114* (2013.01); *A61N 1/025* (2013.01); *A61N 1/378* (2013.01); *A61N 1/08* (2013.01)
USPC ................... 607/62; 607/66; 607/70; 607/71; 607/72; 607/73; 607/74; 607/75; 607/76

(58) Field of Classification Search
USPC ................ 607/6, 15, 52, 45, 46, 66, 70–76, 9
See application file for complete search history.

(56) References Cited

U.S. PATENT DOCUMENTS

| 3,796,221 A | 3/1974 | Hagfors |
| 4,324,251 A | 4/1982 | Mann |
| 4,488,555 A | 12/1984 | Imran |
| 4,556,061 A | 12/1985 | Barreras |
| 4,686,990 A | 8/1987 | Moberg |
| 4,702,254 A | 10/1987 | Zabara |
| 4,715,381 A | 12/1987 | Moberg |
| 4,850,356 A | 7/1989 | Heath |
| 4,867,164 A | 9/1989 | Zabara |
| 4,899,750 A | 2/1990 | Ekwall |
| 4,964,407 A | 10/1990 | Baker et al. |
| 5,025,807 A | 6/1991 | Zabara |
| 5,127,404 A | 7/1992 | Wyborny et al. |
| 5,137,020 A | 8/1992 | Wayne et al. |

(Continued)

FOREIGN PATENT DOCUMENTS

| WO | 0108749 | 2/2001 |
| WO | 2004075982 | 9/2004 |

OTHER PUBLICATIONS

Terry, R.S., et al., "The Implantable Neurocybernetic Prosthesis System," Pacing and Clinical Electrophysiology, vol. 14, No. 1, (Jan. 1991), pp. 86-93.

(Continued)

*Primary Examiner* — Michael Kahelin
*Assistant Examiner* — Mallika D Fairchild
(74) *Attorney, Agent, or Firm* — Cyberonics, Inc.

(57) ABSTRACT

A method comprises applying a first open-loop electrical signal to a neural structure at a first rate. The method also comprises applying a closed-loop electrical signal to the neural structure in response to an event detection, thus causing an overall rate at which electrical stimulation is applied to the neural structure to exceed the first rate. The method further comprises applying a second open-loop electrical signal to a neural structure at a second rate that is lower than the first rate, thus causing the overall rate to be reduced to the first rate.

20 Claims, 7 Drawing Sheets

(56) References Cited

U.S. PATENT DOCUMENTS

| | | |
|---|---|---|
| 5,137,021 A | 8/1992 | Wayne et al. |
| 5,146,920 A | 9/1992 | Yuuchi et al. |
| 5,154,172 A | 10/1992 | Terry, Jr. et al. |
| 5,179,950 A | 1/1993 | Stanislaw |
| 5,188,104 A | 2/1993 | Wernicke et al. |
| 5,193,538 A | 3/1993 | Ekwall |
| 5,201,808 A | 4/1993 | Steinhaus et al. |
| 5,201,865 A | 4/1993 | Kuehn |
| 5,215,086 A | 6/1993 | Terry, Jr. et al. |
| 5,222,494 A | 6/1993 | Baker, Jr. |
| 5,231,988 A | 8/1993 | Wernicke et al. |
| 5,263,480 A | 11/1993 | Wernicke et al. |
| 5,269,303 A | 12/1993 | Wernicke et al. |
| 5,299,569 A | 4/1994 | Wernicke et al. |
| 5,330,515 A | 7/1994 | Rutecki et al. |
| 5,335,657 A | 8/1994 | Terry, Jr. et al. |
| 5,344,431 A | 9/1994 | Merritt et al. |
| 5,352,962 A | 10/1994 | Galburt |
| 5,352,968 A | 10/1994 | Reni et al. |
| 5,372,607 A | 12/1994 | Stone et al. |
| 5,391,193 A | 2/1995 | Thompson |
| 5,431,692 A | 7/1995 | Hansen et al. |
| 5,458,624 A | 10/1995 | Renirie et al. |
| 5,496,353 A | 3/1996 | Grandjean et al. |
| 5,507,786 A | 4/1996 | Morgan et al. |
| 5,522,865 A | 6/1996 | Schulman et al. |
| 5,534,018 A | 7/1996 | Wahlstrand et al. |
| 5,540,730 A | 7/1996 | Terry, Jr. et al. |
| 5,540,734 A | 7/1996 | Zabara |
| 5,549,646 A | 8/1996 | Katz et al. |
| 5,571,150 A | 11/1996 | Wernicke et al. |
| 5,620,474 A | 4/1997 | Koopman |
| 5,703,469 A | 12/1997 | Kinoshita |
| 5,707,400 A | 1/1998 | Terry, Jr. et al. |
| 5,713,936 A | 2/1998 | Staub |
| 5,741,307 A | 4/1998 | Kroll |
| 5,741,311 A | 4/1998 | McVenes et al. |
| 5,755,742 A | 5/1998 | Schuelke et al. |
| 5,769,873 A | 6/1998 | Zadeh |
| 5,814,088 A | 9/1998 | Paul et al. |
| 5,876,425 A | 3/1999 | Gord et al. |
| 5,891,179 A | 4/1999 | Er et al. |
| 5,897,577 A | 4/1999 | Cinbis et al. |
| 5,925,068 A | 7/1999 | Kroll |
| 5,928,272 A | 7/1999 | Adkins et al. |
| 6,016,448 A | 1/2000 | Busacker et al. |
| 6,073,050 A | 6/2000 | Griffith |
| 6,108,579 A | 8/2000 | Snell et al. |
| 6,148,235 A | 11/2000 | Kuiper |
| 6,167,309 A | 12/2000 | Lyden |
| 6,181,969 B1 | 1/2001 | Gord |
| 6,185,461 B1 | 2/2001 | Er |
| 6,212,431 B1 | 4/2001 | Hahn et al. |
| 6,317,633 B1 | 11/2001 | Jorgenson et al. |
| 6,341,236 B1 | 1/2002 | Osorio et al. |
| 6,400,988 B1 | 6/2002 | Gurewitsch |
| 6,445,951 B1 | 9/2002 | Mouchawar |
| 6,453,198 B1 | 9/2002 | Torgerson et al. |
| 6,473,644 B1 | 10/2002 | Terry, Jr. et al. |
| 6,490,484 B2 | 12/2002 | Dooley et al. |
| 6,490,486 B1 | 12/2002 | Bradley |
| 6,553,263 B1 | 4/2003 | Meadows et al. |
| 6,587,719 B1 | 7/2003 | Barrett et al. |
| 6,587,727 B2 | 7/2003 | Osorio et al. |
| 6,609,025 B2 | 8/2003 | Barrett et al. |
| 6,620,186 B2 | 9/2003 | Saphon et al. |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,631,293 B2 | 10/2003 | Lyden |
| 6,648,823 B2 | 11/2003 | Thompson |
| 6,654,640 B2 | 11/2003 | Lyden |
| 6,658,294 B1 | 12/2003 | Zadeh et al. |
| 6,662,053 B2 | 12/2003 | Borkan |
| 6,671,552 B2 | 12/2003 | Merritt et al. |
| 6,671,556 B2 | 12/2003 | Osorio et al. |
| 6,687,538 B1 | 2/2004 | Hrdlicka et al. |
| 6,721,600 B2 | 4/2004 | Jorgenson et al. |
| 6,745,077 B1 | 6/2004 | Griffith et al. |
| 6,748,273 B1 | 6/2004 | Obel et al. |
| 6,760,624 B2 | 7/2004 | Anderson et al. |
| 6,760,625 B1 | 7/2004 | Kroll |
| 6,804,557 B1 | 10/2004 | Kroll |
| 6,820,019 B1 | 11/2004 | Kelly et al. |
| 6,901,293 B2 | 5/2005 | Rogers et al. |
| 6,940,255 B2 | 9/2005 | Loch |
| 7,142,923 B2 | 11/2006 | North et al. |
| 7,174,213 B2 * | 2/2007 | Pless ................... 607/45 |
| 7,254,444 B2 | 8/2007 | Moore et al. |
| 7,584,000 B2 * | 9/2009 | Erickson ............... 607/46 |
| 7,751,891 B2 | 7/2010 | Armstrong et al. |
| 7,904,161 B2 | 3/2011 | Osypka |
| 2001/0034541 A1 | 10/2001 | Lyden |
| 2002/0022866 A1 | 2/2002 | Borkan |
| 2003/0074037 A1 | 4/2003 | Moore |
| 2004/0039424 A1 | 2/2004 | Merritt et al. |
| 2004/0199146 A1 | 10/2004 | Rogers et al. |
| 2005/0088145 A1 | 4/2005 | Loch |
| 2005/0177206 A1 | 8/2005 | North et al. |
| 2005/0272280 A1 | 12/2005 | Osypka |
| 2007/0150019 A1 | 6/2007 | Youker et al. |
| 2007/0216366 A1 | 9/2007 | Inamine et al. |
| 2007/0255374 A1 * | 11/2007 | Kolafa et al. ........... 607/118 |
| 2008/0097544 A1 | 4/2008 | Gandhi |
| 2010/0121591 A1 | 5/2010 | Hall |

OTHER PUBLICATIONS

Woodbury, J.W. et al., "Vagal Stimulation Reduces the Severity of Maximal Electroshock Seizures in Intact Rats: Use of Cuff Electrode for Stimulating and Recording," PACE, vol. 14, (Jan. 1991), pp. 94-107.

International Application No. PCT/US2007/000337, Written Opinion dated Jul. 27, 2008, 8 pgs.

International Application No. PCT/US2005/026514, Written Opinion dated Oct. 10, 2006, 4 pgs.

International Patent Application No. PCT/US2011/061003, International Search Report and Written Opinion dated Jun. 28, 2012, 10 pages.

* cited by examiner

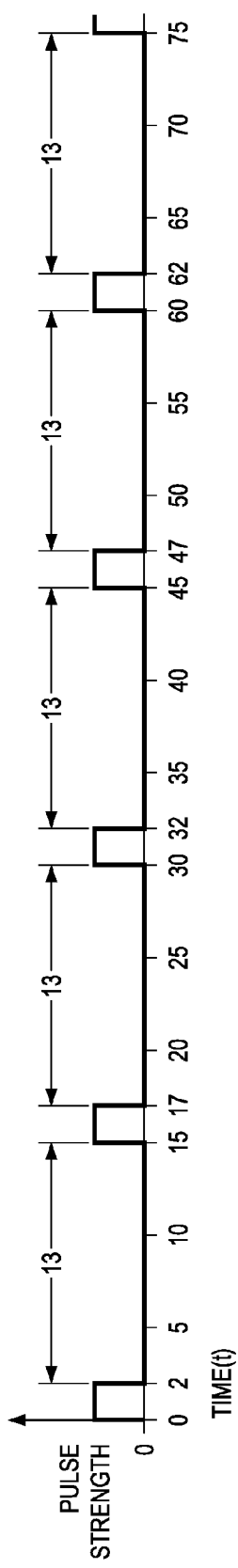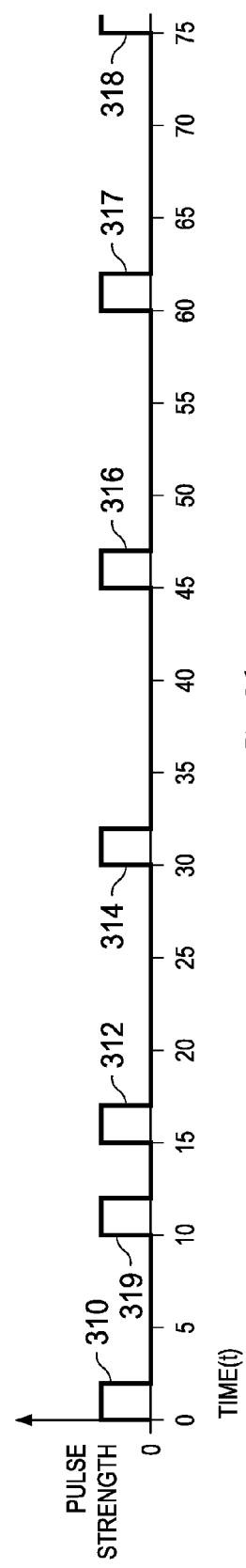
FIG. 3a (PRIOR ART)
FIG. 3b (PRIOR ART)

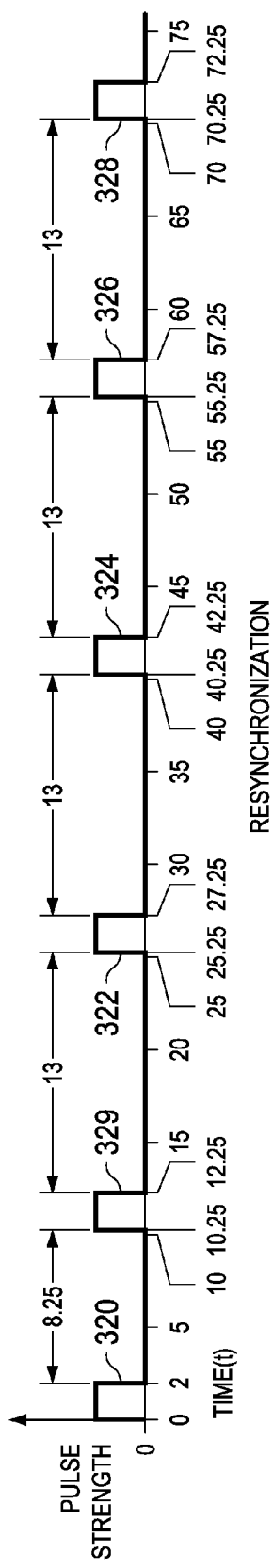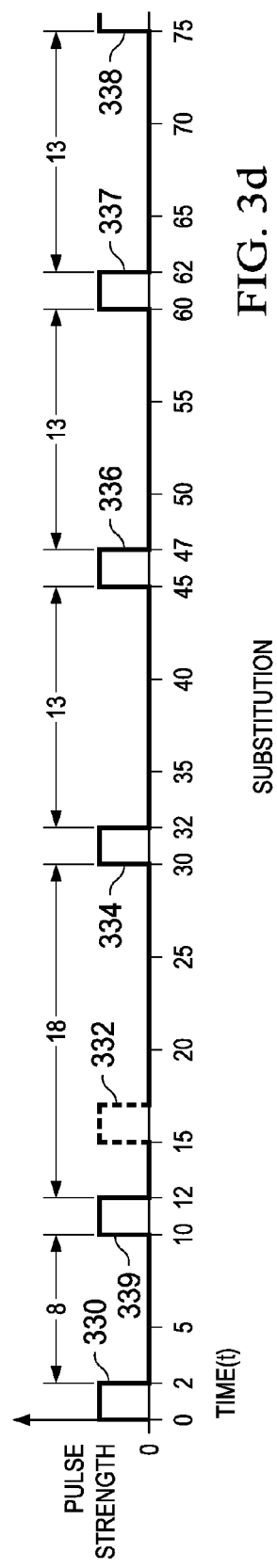

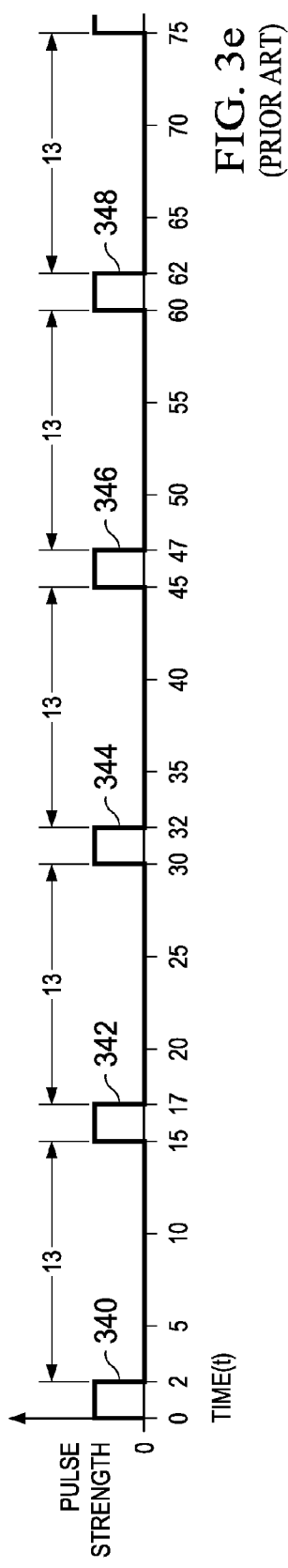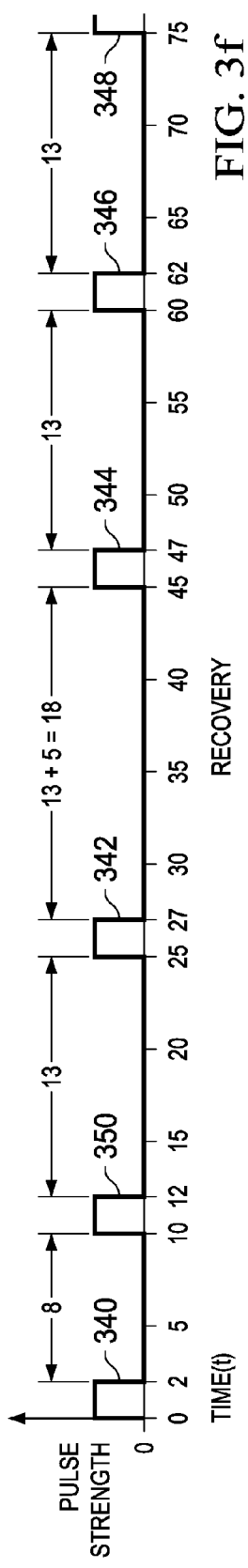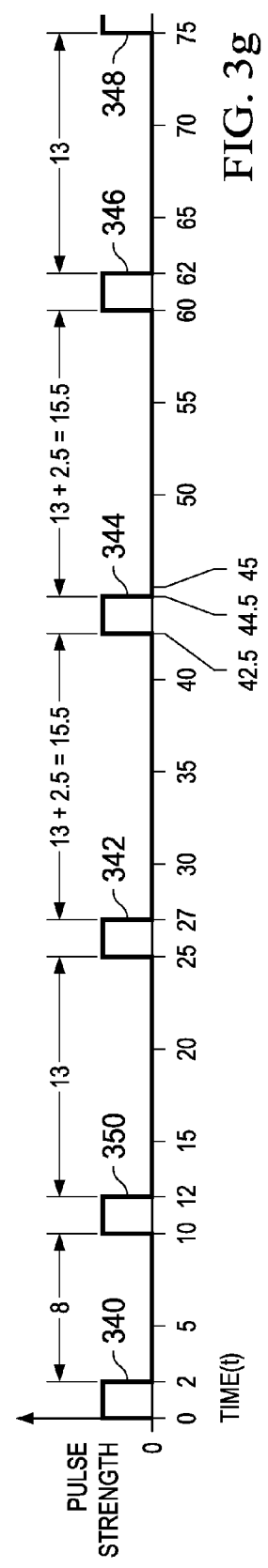

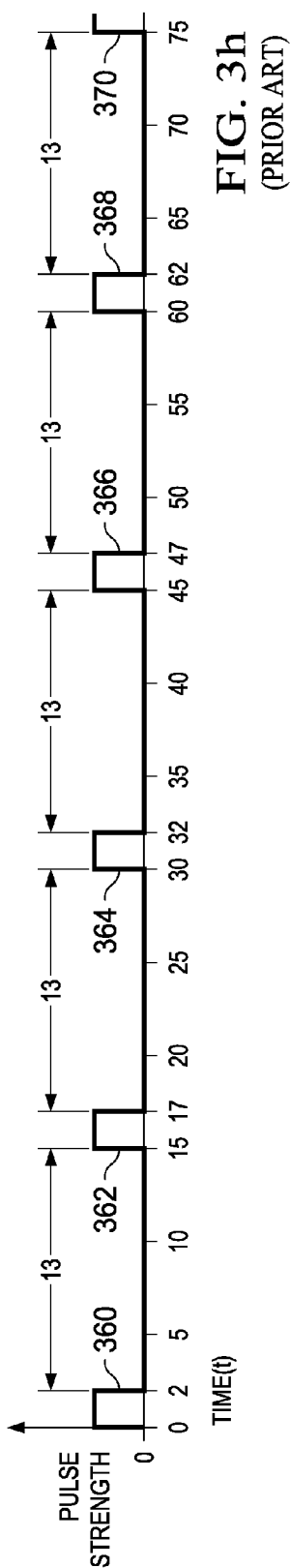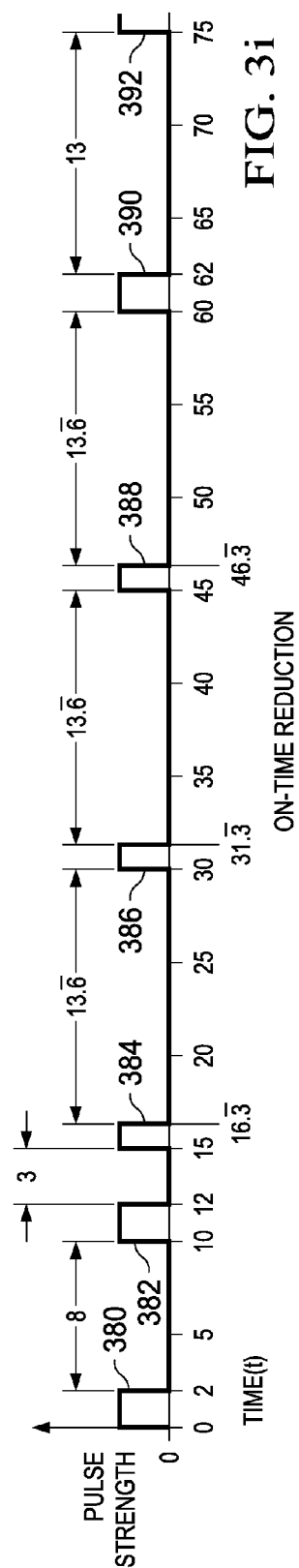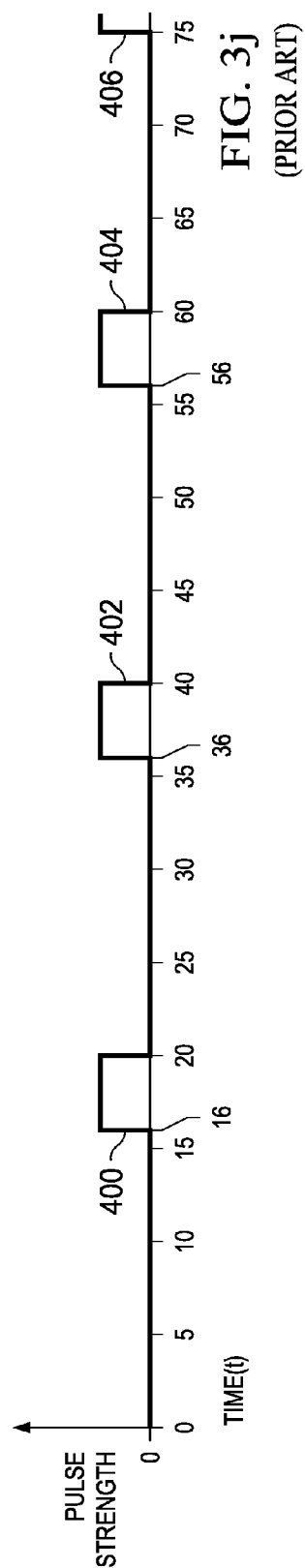

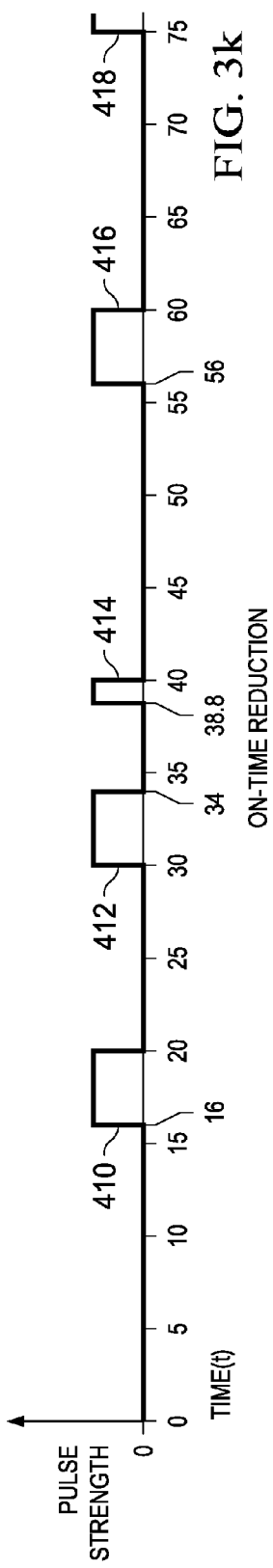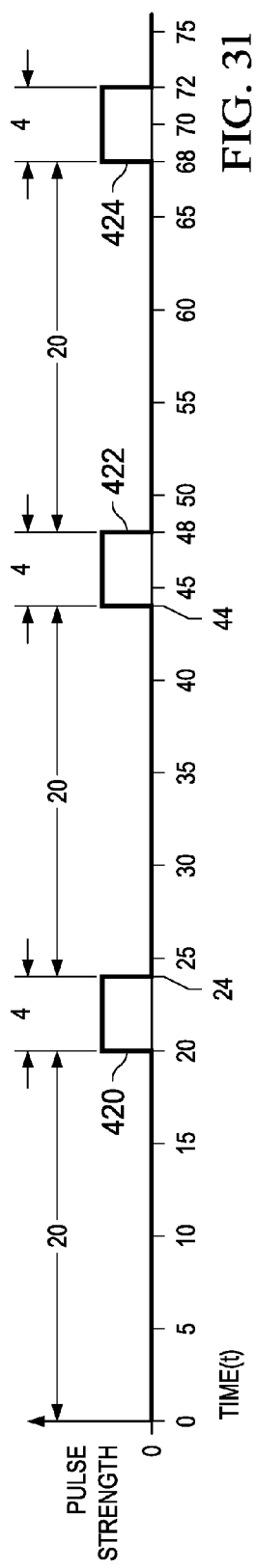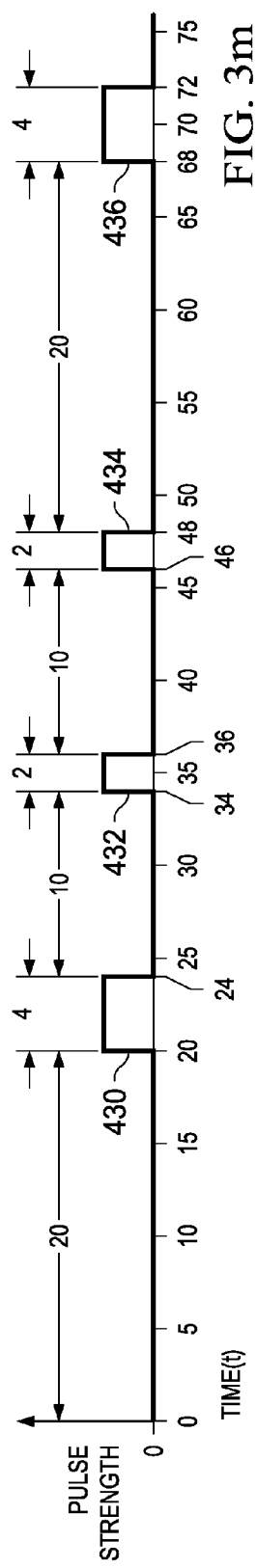

DELIVERING SCHEDULED AND UNSCHEDULED THERAPY WITHOUT DETRIMENT TO BATTERY LIFE OR ACCURACY OF LONGEVITY PREDICTIONS

BACKGROUND

Medical treatments for disorders of the nervous system, such as seizure disorders (e.g., epilepsy), have improved in recent decades. One available treatment involves the application of an electrical signal to reduce various symptoms or effects caused by such neural disorders. For example, electrical signals have been successfully applied at strategic locations in the human body to provide various benefits, including a reduction of seizure occurrence and the improvement of other medical conditions. An example of such a treatment regimen involves the application of electrical stimulation to the vagus nerve of the human body to reduce or eliminate epileptic seizures, as described in U.S. Pat. No. 4,702,254, which is incorporated herein by reference.

Electrical stimulation of a target tissue of a patient's body may be provided by implanting an electrical device (known as an implantable medical device, or IMD) underneath the skin of a patient and electrically stimulating the target tissue. In some cases, electrical stimulation of target tissue (including, but not limited to neural tissue such as the vagus nerve) may be delivered in accordance with a programmed (or predetermined or "planned") schedule. In such cases, the electrical stimulation is referred to as "open-loop," "passive," or "non-feedback" stimulation. In other cases, electrical stimulation may be delivered in response to detecting some type of event. In one embodiment, the event may be patient-initiated. In another embodiment, the event may be detecting a change in one or more body parameters (for example, cardiac rhythm, muscle activity, or body movements). Typically, the parameter(s) is selected such that the change is indicative of a disease state such as an epileptic seizure. This type of stimulation is known as "closed-loop," "active" or "feedback" stimulation. In some devices, both open-loop and closed-loop stimulation may be simultaneously employed, with an open-loop program operating to provide a basic level of therapy and closed-loop stimulation provided in response to episodic events.

Whether delivered as closed-loop or open-loop, the stimulation is typically applied as a sequence of pulses (collectively referred to as a "burst") extending for a defined duration (known as the "on-time" or "burst duration"). In open-loop stimulation, the pulse bursts are separated by a programmed time period (the "off-time"), and in closed-loop stimulation the bursts are delivered in response to the detected event and may include a refractory period after the closed-loop burst to allow the nerve to recover. During the on-time of a pulse burst, electrical pulses of a defined electrical current (e.g., 0.5-3.5 milliamps) and pulse width (e.g., 0.25-1.0 milliseconds) are delivered at a defined frequency (e.g., 20-30 Hz) for the burst duration (e.g., 7-60 seconds). For open-loop stimulation, the on-time and off-time parameters together define a duty cycle, which is the ratio of the on-time to the combination of the on-time and off-time, and which describes the percentage of time that the electrical signal is applied to the nerve.

Most IMDs are powered by batteries; consequently, the amount of power available to them is finite. Just before the battery of an IMD is exhausted, the IMD must be surgically removed from a patient's body so that a new device (or battery) may be installed. For this reason, the ability to accurately predict a battery's remaining life is crucial to ensuring that therapy to the patient is not interrupted, which may endanger the patient's health. Overestimating an IMD's battery life can result in interruption of therapy by precluding timely replacement of the IMD and/or battery prior to exhaustion of its electrical charge. One the other hand, underestimating an IMD's battery life can result in surgery that is not necessary at that time and a waste of the useful life of the IMD.

Predicting battery life generally is relatively uncomplicated when an IMD only applies electrical pulses in accordance with a planned schedule ("open-loop" stimulation). When closed-loop stimulation is used (either alone or in combination with open-loop stimulation), predicting battery life becomes difficult, because closed-loop stimulation is patient-specific and does not occur according to any predetermined schedule. Further, delivering closed-loop stimulation in addition to scheduled, open-loop stimulation may result not only in overstimulation but also may substantially reduce battery life.

Thus, methods and systems for conserving, extending and accurately predicting battery life in IMDs that apply closed-loop stimulation are desired.

BRIEF DESCRIPTION OF THE DRAWINGS

For a detailed description of exemplary embodiments of the invention, reference will now be made to the accompanying drawings in which:

FIGS. 3a-3m show various patterns of stimulation that the implantable medical device of FIG. 2 may provide, consistent with embodiments of the invention;

NOTATION AND NOMENCLATURE

Figure 1:
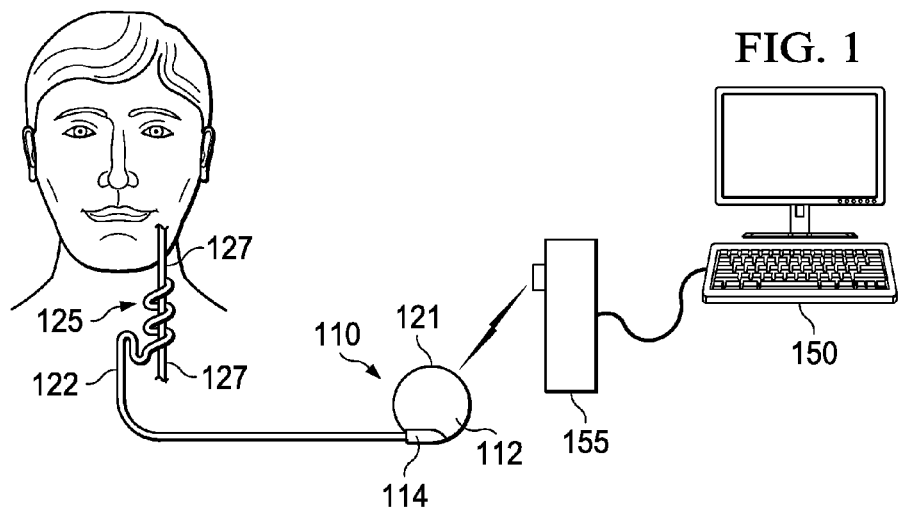
FIG. 1 shows an illustrative stimulation system coupled to a human cranial nerve, consistent with embodiments of the invention.

Certain terms are used throughout the following description and claims to refer to particular system components. As one skilled in the art will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct electrical connection. Thus, if a first device couples to a second device, that connection may be through a direct electrical connection, or through an indirect electrical connection via other devices and connections.

DETAILED DESCRIPTION

The following discussion is directed to various embodiments of the invention. Although one or more of these embodiments may be preferred, the embodiments disclosed should not be interpreted, or otherwise construed, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Disclosed herein are various techniques for conserving, extending and accurately predicting battery life in an implantable medical device (IMD) that delivers both open-loop and closed-loop electrical stimulation. Techniques for conserving and extending battery life are described first, followed by a description of techniques for accurately predicting battery life.

In some battery life conservation embodiments of the present invention, the predetermined schedule at which open-loop stimulation is to be administered is dynamically adjusted to compensate for any closed-loop stimulation burst that is provided outside the predetermined open-loop schedule. For example, in some of these embodiments, a closed-loop stimulation burst may cause the open-loop stimulation schedule to be "reset" so that open-loop stimulation bursts are delivered as scheduled, but with the schedule "resynchronized" to provide subsequent open-loop bursts based upon the closed-loop stimulation burst rather than the immediately preceding open-loop burst. In some embodiments, a closed-loop stimulation burst may cause the next planned open-loop stimulation burst to be skipped, such that the closed-loop burst is "substituted" for the skipped open-loop burst. In some embodiments, a closed-loop stimulation burst may be compensated for by increasing the length of one or more off-time cycles following the closed-loop stimulation burst; similarly, in some embodiments, a closed-loop stimulation burst may be compensated for by decreasing the length of one or more scheduled stimulation bursts following the closed-loop stimulation burst. In some cases, one or more of the foregoing techniques may be combined. Various embodiments are now described in detail with reference to the figures.

FIG. 1 illustrates an implantable medical device (IMD) 110 having a main body 112 comprising a can 121 with a connector 114 for connecting to leads 122. The IMD 110 is implanted in a patient's chest in a pocket or cavity formed by the implanting surgeon just below the skin, similar to the implantation procedure for a pacemaker pulse generator. A stimulating nerve electrode assembly 125, preferably comprising an electrode pair, conductively couples to the distal end of an insulated and electrically conductive lead assembly 122, which preferably comprises a pair of lead wires (one wire for each electrode of an electrode pair). Lead assembly 122 is attached at its proximal end to the connector 114 on can 121. The electrode assembly is surgically coupled to a cranial nerve, such as a vagus nerve 127 in the patient's neck. The electrode assembly 125 preferably comprises a bipolar stimulating electrode pair, such as the electrode pair described in U.S. Pat. No. 4,573,481, which is incorporated herein by reference. Persons of skill in the art will appreciate that many electrode designs could be used in the present disclosure. The two electrodes are preferably wrapped around the vagus nerve, and the electrode assembly 125 preferably is secured to the nerve 127 by a spiral anchoring tether such as that disclosed in U.S. Pat. No. 4,979,511, which is incorporated herein by reference. Lead assembly 122 may be secured, while retaining the ability to flex with movement of the chest and neck, by a suture connection to nearby tissue.

The IMD 110 may be controlled or programmed with an external device 150 (e.g., a computer) and a programming wand 155 to facilitate radio frequency (RF) communication between the external device 150 and the IMD 110. The wand 155 and software permit noninvasive communication with the IMD 110 after the latter is implanted. In systems where the external device 150 uses one or more channels in the Medical Implant Communications Service (MICS) bandwidths, the programming wand 155 may be omitted to permit more convenient communication directly between the external device 150 and the IMD 110.

Figure 2:
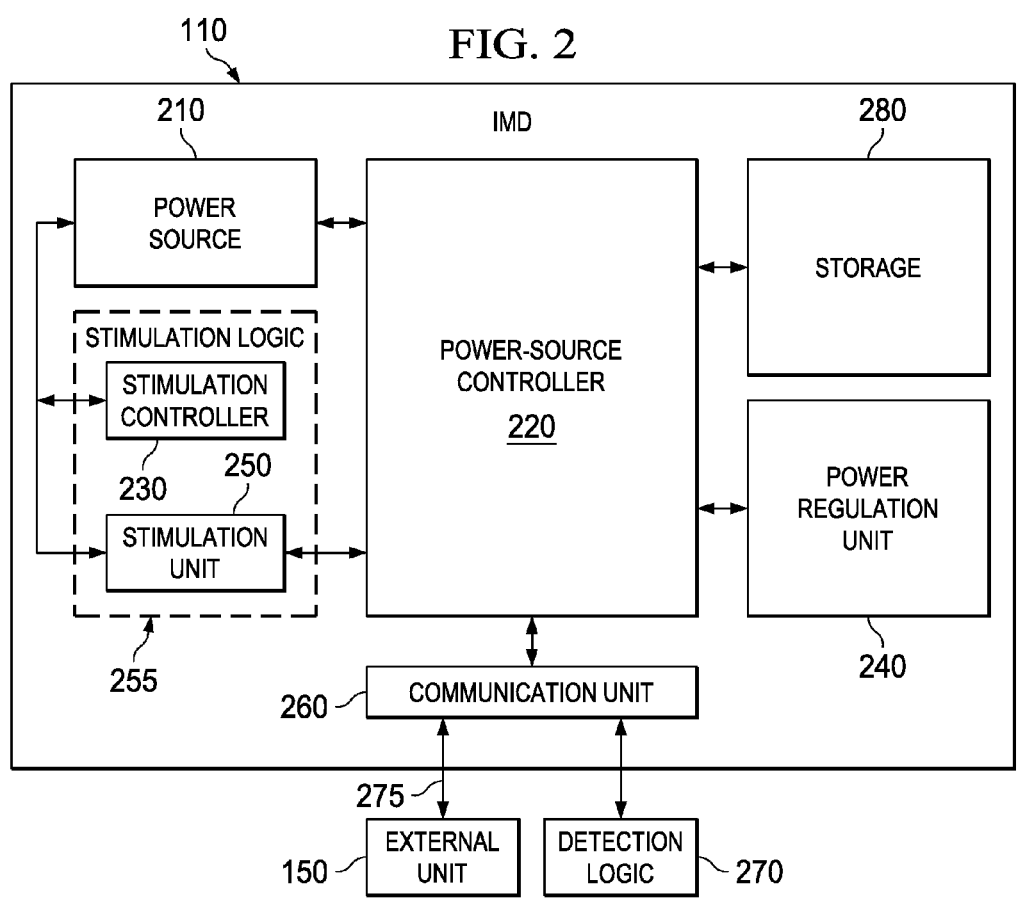
FIG. 2 shows a block diagram of the implantable medical device shown in FIG. 1, consistent with embodiments of the invention.

FIG. 2 illustrates a block diagram of IMD 110 for performing neurostimulation in accordance with embodiments of the present disclosure. In one embodiment, the IMD 110 comprises a power source 210, a power-source controller 220, a stimulation controller 230, a power regulation unit 240, a stimulation unit 250, a communication unit 260 and storage 280. The stimulation controller 230 and stimulation unit 250 together form stimulation logic 255. Storage 280 may be used for storing various program codes, starting data, and the like. The power source 210 may comprise a battery, which may be rechargeable or non-rechargeable. Other power sources, such as capacitors, may also be used. The power source 210 provides power for the operation of the IMD 110, including electronic operations and stimulation bursts. Power source 210, in one embodiment, may be a lithium-thionyl chloride cell or a lithium/carbon monofluoride (LiCFx) cell. The terminals of the power source 210 preferably electrically couple to an input side of the power-source controller 220 and the power regulation unit 240.

The power-source controller 220 preferably comprises circuitry for controlling and monitoring the flow of electrical power to various electronic and stimulation-portions of the IMD 110 (such as the components 230, 240, 250, 260 and 280 illustrated in FIG. 2). More particularly, the power-source controller 220 is capable of monitoring the power consumption or charge depletion of the IMD 110, measuring the voltage across the power source 210, and generating elective replacement and/or end-of-service signals.

The communication unit 260 facilitates communication between the IMD 110 and the external unit 150, as shown. The external unit 150 may be a device that is capable of programming various components and stimulation parameters of the IMD 110. In one embodiment, the external unit 150 is a computer system capable of electronic communications, programming, and executing a data-acquisition program, preferably a handheld computer or PDA. The external unit 150 preferably is controlled by a healthcare provider such as a physician in, for example, a doctor's office. The external unit 150 may be used to download various parameters and program software into the IMD 110 for programming the operation of the IMD. The external unit 150 may also receive and upload various status conditions and other data from the IMD 110. The communication unit 260 may comprise hardware, software, firmware or any combination thereof. Communications between the external unit 150 and the communication unit 260 may occur via a wireless or other type of communication, illustrated generally by line 275 in FIG. 2.

The power regulation unit 240 is capable of regulating power delivered by the power source 210 to particular components of the IMD 110 according to their needs and functions. The power regulation unit 240 may perform a voltage conversion to provide appropriate voltages and/or currents for the operation of the components. The power regulation unit 240 may comprise hardware, software, firmware or any combination thereof. The communication unit 260 is capable of providing transmission and reception of electronic signals to and from an external unit 150.

Stimulation controller 230 defines the electrical stimulation pulses to be delivered as part of a burst to the nerve tissue according to parameters and waveforms that may be programmed into the IMD 110 using the external unit 150 or that may be pre-programmed into the controller 230 prior to or after implantation of the IMD 110 into the patient's body. The stimulation controller 230 controls the operation of the stimulation unit 250, which generates the stimulation pulses comprising a burst according to the parameters defined by the controller 230 and, in some embodiments, provides these pulses to the lead assembly 122 and electrode assembly 125. Stimulation pulses provided by the IMD 110 may vary widely across a range of parameters. The stimulation controller 230 may comprise hardware, software, firmware or any combination thereof.

In some embodiments, the stimulation logic 255 (stimulation controller 230 and stimulation unit 250) delivers stimulation bursts in response to certain events. For example, in some cases, the controller 230 and the unit 250 may deliver a stimulation burst in response to detecting an impending or already-occurring seizure based on one or more of the patient's cardiac parameters (e.g., heart rate, rate of change of heart rate, heart rate variability, etc.). However, detection logic 270 may be implemented anywhere on the patient's body to detect any type of event. In some embodiments, the detection logic 270 may be disposed in a location other than the patient's body to detect some other type of event independent of the patient's body (e.g., a request for a stimulation burst initiated by the patient). Detection logic 270 may include a sensor (e.g., a sensor that detects user input, such as a tap or magnetic input apparatus). Upon detecting an event, the detection logic 270 causes the stimulation controller 230 to activate the stimulation unit 250 in response to the detected event. One or more of the blocks 210-280 may comprise hardware, firmware, software or any combination thereof.

FIGS. 3a-3m show waveforms that represent various ways in which the stimulation controller 230 may cause the stimulation unit 250 to deliver stimulation pulse bursts to the nerve to which the IMD 110 couples. In each of the waveforms of FIGS. 3a-3m, the x-axis represents time and the y-axis represents electrical stimulation strength (e.g., current). The scope of this disclosure is not limited to the stimulation depicted in FIGS. 3a-3m.

FIG. 3a shows a waveform that represents an example of programmed, open-loop stimulation pulse bursts. As shown, during typical, open-loop stimulation with no closed-loop stimulation interruptions, pulse bursts are delivered at regular intervals according to programmed parameters defining the duration of the bursts (i.e., on-time), the current, frequency and pulse width of each pulse within the burst, and the time between each burst (i.e., off-time). In the embodiment depicted in FIG. 3a, each burst lasts for 2 seconds and each programmed off time lasts for 13 seconds. An entire on-time/off-time cycle thus lasts for 15 seconds, with the pulses comprising the burst defined by one or more programmed parameters such as current, pulse width and frequency. The timing can be varied as desired by programming different values for the on-time and the off-time. In such embodiments, electrical stimulation dosing, battery usage and battery life are predictable because all stimulation bursts are delivered according to the programmed parameters in advance of delivery.

FIG. 3b shows a waveform that represents a scheduled, open-loop stimulation burst pattern to which a responsive, closed-loop stimulation burst has been added. Bursts 310, 312, 314, 316, 317 and 318 are scheduled, open-loop stimulation bursts. In contrast, burst 319 is an unscheduled, closed-loop stimulation burst. Stimulation unit 250 delivers the burst 319 as a result of some event, such as, for example, the detection of a particular cardiac change that signals an ongoing or impending seizure. In some embodiments, the burst 319 may be delivered as the result of manual instruction (e.g., the patient waves a magnet near the IMD 110, thereby triggering delivery of the burst 319). However, as shown, despite delivery of the burst 319, the open-loop stimulation bursts are delivered as programmed, just as they were delivered as shown in FIG. 3a. In the scheme shown in FIG. 3b, stimulation dosing, battery usage and battery life all are unpredictable, or poorly predictable. However, therapy for the patient may be improved because closed-loop stimulation bursts are delivered as needed in response to, for example, an acute episodic event such as an epileptic seizure.

FIG. 3c shows an embodiment of the present invention in which a waveform that represents a programmed, open-loop stimulation burst pattern has been modified as the result of introducing an unprogrammed, closed-loop stimulation burst. Electrical stimulation bursts 320, 322, 324, 326 and 328 are programmed, open-loop bursts. Burst 329 is a responsive, closed-loop burst. Burst 320 is delivered at time t=0 and lasts for 2 seconds, until t=2. After t=2, 13 seconds were scheduled to elapse prior to delivery of the next scheduled, open-loop burst—burst 322 (i.e., at t=15). However, instead of the burst 322 being delivered at t=15 seconds, a responsive, closed-loop burst 329 is delivered after an off cycle of only 8.25 seconds (i.e., at t=10.25). This closed-loop burst 329 is delivered on-demand, in response to some event (e.g., detecting an impending seizure, manual stimulation, etc.).

In the embodiment of FIG. 3c, after delivering this unprogrammed, closed-loop burst 329, the IMD 110 reschedules the delivery of the subsequent open-loop bursts 322, 324, 326 and 328, to synchronize them with the responsive, closed-loop burst 329. Specifically, while the open-loop burst 322 was scheduled to be delivered 13 seconds after the end of open-loop burst 320, burst 322 is offset so that it is instead delivered 13 seconds after the end of closed-loop burst 329. Subsequent programmed, open-loop bursts are then delivered after the off-time period following rescheduled burst 322. Thus, while open-loop burst 324 was originally scheduled to be delivered 28 seconds after the end of the programmed, open-loop burst 320, burst 324 is instead delivered 28 seconds after the end of closed-loop burst 329 (i.e., 13 seconds after the end of the rescheduled burst 322). Bursts 326 and 328 are similarly synchronized to be applied 13 seconds after the previous (rescheduled) burst. In the embodiment of FIG. 3c, therefore, all subsequent open-loop bursts following an unprogrammed, closed-loop burst are resynchronized to occur at the programmed off-time intervals following the closed-loop burst, rather than occurring the programmed off-time intervals following the open-loop burst that immediately precedes the closed-loop burst. The technique depicted in FIG. 3c allows for delivery of responsive, closed-loop therapy bursts while preventing subsequent scheduled, open-loop therapy bursts from being administered unnecessarily early. The embodiment of FIG. 3c will impose an increased battery life cost on the IMD by the sum of the times that each responsive, closed-loop stimulation burst is delivered before the next scheduled, open-loop burst. This time interval may be referred to as "early intervention time" or EIT.

FIG. 3d shows a waveform that represents another scheduled, open-loop stimulation burst pattern that has been modified as the result of introducing an unprogrammed, closed-loop stimulation burst. Electrical stimulation bursts 330, 332, 334, 336, 337 and 338 are programmed, open-loop bursts. Burst 339 is a responsive, closed-loop burst. Burst 330 is delivered at time t=0 and lasts for 2 seconds, until t=2. After t=2, 13 seconds were scheduled to elapse prior to delivery of the next programmed, open-loop burst 332 (i.e., at t=15). Similarly, open-loop burst 334 was scheduled for delivery 13 seconds after the end of burst 332, and so on. However, instead of the burst 332 being delivered at t=15 seconds, an unscheduled, closed-loop burst 339 is delivered in response to an event. As a result of the delivery of this burst 339, scheduling for the open-loop bursts is adjusted. In particular, as a result of delivering the responsive, closed-loop burst 339 prior to programmed burst 332, the IMD 110 skips delivery of burst 332 so that the programmed, open-loop burst 334 is the next burst to be delivered after the closed-loop burst 339. Moreover, in the embodiment of FIG. 3d, burst 334 is delivered at its programmed time, and is unaffected in terms of its timing, by the delivery of closed-loop burst 339. In this way, the total electrical stimulation dosage delivered to the patient remains unchanged from the completely open-loop dosage, despite the periodic occurrence of responsive, closed-loop bursts. In addition to ensuring that the patient is not overdosed, this technique increases predictability of battery life determinations while providing the benefits of on-demand, closed-loop therapy. By considering the responsive, closed-loop burst 339 as a substitute for the next scheduled open-loop burst 332, the embodiment of FIG. 3d will provide improved battery life over the embodiment of FIG. 3c, because it does not involve the accumulation of EIT. If the burst parameters defining the closed-loop burst 339 are identical to those of the open-loop burst 332 for which it is substituted, the embodiment of FIG. 3d will provide battery life essentially identical to that of purely open-loop stimulation as depicted in FIG. 3a.

FIGS. 3e-3g show other techniques in accordance with various embodiments. FIG. 3e illustrates a waveform of another scheduled, open-loop stimulation burst pattern. Specifically, FIG. 3e depicts scheduled, open-loop bursts 340, 342, 344, 346 and 348. Each pulse lasts for 2 seconds and is followed by an off-time that lasts for 13 seconds. Thus, pulse 340 begins at t=0 and lasts until t=2, at which time an off-time begins and lasts until t=15. At t=15, pulse 342 begins, and so forth.

FIGS. 3f and 3g illustrate alternative approaches to the "resynchronization" approach of FIG. 3c and the "substitution" approach of FIG. 3d. More particularly, the approaches outlined in FIGS. 3f and 3g permit "recovery" of the time period by which a closed-loop burst is delivered before the next scheduled, open-loop burst. In other words, the FIGS. 3f and 3g depict recovery of the early intervention time (EIT) associated with closed-loop stimulation bursts. FIG. 3f depicts the introduction of an unprogrammed, closed-loop burst 350 (e.g., in response to detection of an event or impending event). Specifically, at t=10, a responsive, closed-loop burst 344 is delivered as a result of the IMD 110 detecting an event. Thus, the IMD 110 delivers a responsive burst (i.e., burst 350) 5 seconds before the IMD 110 is scheduled to deliver a burst (i.e., programmed burst 342, as shown in FIG. 3e). To maintain consistent total dosage over time, these 5 seconds of EIT may be added back into the schedule by interspersing them among one or more off cycles between programmed, open-loop bursts.

FIG. 3f shows one example of such interspersion. As shown in FIG. 3f, in some embodiments, after the responsive burst 350, the next programmed burst 342 may be resynchronized to begin after the programmed off-time has elapsed following the responsive burst 350, as in FIG. 3c. After resynchronizing the programmed bursts following the responsive burst 350, the EIT (i.e., the duration of time prior to the scheduled open-loop burst that the responsive, closed-loop burst was delivered) may be recovered by adding all 5 seconds of the EIT back into the open-loop stimulation burst schedule immediately after the first open-loop burst 342 is administered after the programmed off-time following the closed-loop burst 350 (instead of its delivery as originally scheduled after the programmed off-time following the immediately preceding open-loop burst 340). Thus, while open-loop burst 342 was originally scheduled to be delivered at t=15 (as shown in FIG. 3e), insertion of the closed-loop burst 350 and the 13-second off cycle associated therewith causes the open-loop burst 342 to be delivered at t=25. Thereafter, the off-time following the open-loop burst 342 is increased by 5 seconds (from 13 seconds to a total of 18 seconds) to allow for recovery of the 5 seconds of EIT associated with delivery of the closed-loop burst 350. Thus, instead of being delivered at t=40 (as would have been the case had the 5 seconds of EIT not been added to the off-time following burst 342), the open-loop burst 344 is delivered at t=45, as originally programmed and scheduled, as illustrated in FIG. 3e. As a result of this technique, the total number of bursts (i.e., 5 bursts) delivered over the extended period of time shown in FIGS. 3e-3f remains the same regardless of whether the responsive, closed-loop burst 344 is delivered or not. Stated another way, although the burst 350 was unscheduled, the technique of recovering the EIT associated with a responsive stimulation burst places the schedule "back on track" to the programmed open-loop schedule by t=45 (compare the timing of bursts 346 and 348 in FIG. 3e to the timing of bursts 344 and 346 in FIG. 3f, respectively). The total number of bursts delivered between t=0 and t=45 remains the same, regardless of whether the closed-loop burst 350 is delivered or not (compare the first 4 bursts in FIG. 3e with the first 4 bursts in FIG. 3f). In some embodiments, the 5 seconds of EIT may be added to the off-time between bursts 350 and 342 or any other pair of bursts.

In FIG. 3f, the entire EIT of 5 seconds is added as a "lump sum" into the single off-time period following open-loop burst 342. In some embodiments, however, the EIT of 5 seconds may be distributed in smaller quantities over a greater number of off-time cycles. Generally, in such embodiments, 5/n seconds of the EIT are added to each of n off-time cycles. Thus, 5/2 seconds are added to each of 2 off-time cycles; 5/3 seconds are added to each of 3 off-time cycles, and so forth, until the entire EIT period associated with a particular closed-loop burst has been recovered, and the total number of bursts provided is the same as would have been the case had the closed-loop burst not been applied, and only the programmed, open-loop bursts provided. This technique may be generalized by stating that, in such embodiments, x/n seconds are added to each of n off-time cycles, where x represents the early intervention time (EIT). This expression assumes an even distribution of EIT over multiple off-time cycles but, in some embodiments, such distribution of EIT over off-time cycles may be adjusted so that it is uneven (e.g., of a total of 5 seconds EIT, 3 seconds may be added to one off cycle, while 2 seconds are added to another off cycle). It will be appreciated in view of the foregoing disclosure that various mathematical sequences (e.g., linearly increasing, exponentially increasing, random, etc.) may be employed to recover the EIT over a desired number of off-time cycles.

FIG. 3g depicts at least one such embodiment in which 5/2 seconds are added to each of 2 off cycles. The technique shown in FIG. 3g is similar to that shown in FIG. 3f, with one difference. In FIG. 3f, the 5 second EIT is added to the off-time following open-loop burst 342. In contrast, FIG. 3g shows the 5 second EIT being distributed across the next two (2) off-time cycles, i.e., the off-times periods following open-loop bursts 342 and 344. Because the 5 second delay is distributed across 2 off-time cycles instead of just 1 off-time cycle, 5/2 seconds are added to each of the off-time cycles.

Thus, as shown, 2.5 seconds are added to the off-time following burst 342 and another 2.5 seconds are added to the off-time following burst 344. The technique of FIG. 3f gets the burst deliveries "back on schedule" faster than does the technique of FIG. 3g. For instance, FIG. 3f shows the 4$^{th}$ burst in the series being delivered at the same time (t=45) as the 4$^{th}$ burst in the series of FIG. 3e. In contrast, the technique of FIG. 3g does not get the burst deliveries "back on schedule" until t=60, when the 5$^{th}$ burst in the series is delivered at the same time as is the 5$^{th}$ burst in the series of FIG. 3e. It should be noted that instead of distributing the 2.5 second EIT installments among the off-times between bursts 342 and 346, as shown in FIG. 3g, the 2.5 second installments may be distributed among the off-times between bursts 350 and 344 or among off-times between any number of bursts following closed-loop burst 350.

FIGS. 3h-3i depict another technique of compensating for reduced battery life associated with application of a responsive, closed-loop burst in accordance with various embodiments of the present invention. More particularly, in this technique, open-loop bursts that follow a closed-loop burst are shortened to compensate for the extra dosing (i.e., additional electrical charge applied to the target tissue) introduced by the closed-loop burst. This contrasts with the technique of "recovery of EIT" illustrated in FIGS. 3f and 3g by focusing on recovery of the extra electrical charge (as represented by individual pulses within a pulse burst) applied to the nerve in the responsive, closed-loop burst.

More generally, the embodiment of FIG. 3i (and FIG. 3k, discussed hereafter, and other similar but non-illustrated embodiments) adjust a programmed, open-loop electrical signal to compensate for the occurrence of a responsive, closed-loop burst by reducing the amount of charge delivered to the nerve in one or more open-loop bursts following the closed-loop burst, until the total amount of charge delivered in the closed-loop burst has been completely "recovered" from the following closed-loop bursts. This concept of recovering closed-loop charge (CLC) is similar to that of the recovery of EIT discussed earlier (which is a specific embodiment of the more general concept of CLC recovery). In other words, the scheduled delivery of charge in a programmed, open-loop signal is reduced such that the charge delivered in a responsive, closed-loop burst merely substitutes for charge that would otherwise have been delivered as part of the programmed, open-loop signal. In this manner, closed-loop bursts do not increase the amount of charge applied to the nerve (and thus removed from the battery of the IMD) beyond that already programmed to occur under the programmed, open-loop signal. Instead, the delivery of a closed-loop burst simply alters the timing of the delivery of charge to the nerve, not its rate over longer time periods.

FIG. 3h shows a dosing pattern including only programmed, open-loop pulse bursts. Specifically, FIG. 3h depicts scheduled, open-loop bursts 360, 362, 364, 366, 368 and 370. Each burst lasts for 2 seconds and is followed by an off-time that lasts for 13 seconds. Thus, burst 360 begins at t=0 and lasts until t=2, at which time an off-time begins and lasts until t=15. At t=15, pulse 362 begins, and so forth.

FIG. 3i is similar to the pattern of FIG. 3h but includes a responsive, closed-loop burst 382. The closed-loop charge (CLC) introduced by the closed-loop burst 382 is compensated for by reducing the electrical charge delivered to the target tissue during one or more subsequent open-loop bursts. For example, as shown, each of the open-loop bursts 384, 386 and 388 is reduced in duration from 2 seconds to 4/3 seconds (i.e., in each of the subsequent bursts, the programmed on-time of 2 seconds is reduced by ⅔ seconds). By reducing the duration of each of three open-loop pulses by one-third of the programmed on-time, a portion of the CLC associated with closed-loop burst 382 is mitigated. Such CLC recovery may be performed in a variety of ways (e.g., by reducing the durations of any suitable number of bursts by any appropriate amount, which may involve performing reductions on any of a variety of bursts (including closed-loop and open-loop bursts), etc.).

FIG. 3k depicts another technique of compensating for reduced battery life associated with application of a responsive, closed-loop burst in accordance with various embodiments of the present invention. In this technique, the duration of an off-time that precedes a burst dictates the duration of that burst. By adjusting burst (i.e., on-time) duration in accordance with the off-time duration preceding it, desired duty cycles (defined as the ratio of on-time to the sum of on-time and off-time) are maintained despite the introduction of responsive, closed-loop bursts.

FIG. 3j shows a dosing pattern including only scheduled, open-loop bursts. Specifically, FIG. 3j depicts scheduled, open-loop bursts 400, 402, 404 and 406. Each burst lasts for 4 seconds and is preceded by an off-time that lasts for 16 seconds. Thus, an off-time begins at t=0 and lasts until t=16, at which time an open-loop burst 400 begins and lasts until t=20. At t=20, the next off-time begins, and so forth. By alternating 4 second on-times with 16 second off-times, an on-time to off-time ratio of 1:4 is achieved and maintained.

FIG. 3k shows a pattern similar to that of FIG. 3j except it includes a responsive, closed-loop burst 412. To allow for recovery of the CLC delivered by closed-loop burst 412, the next scheduled, open-loop burst 414 is generated at its scheduled time, but the duration (i.e., on-time) of burst 414 is adjusted to be in proportion with the duration of the off-time between the closed-loop burst 412 and the open-loop burst 414. In this example, the off-time between bursts 412 and 414 is 4.8 seconds, and the desired on-time to off-time ratio is 1:4. Thus, the pulse 414 is adjusted to be only 1.2 seconds in duration, since 1.2/4.8=¼. The next open-loop pulse 416 is delivered on schedule and is of the programmed duration. In the example of FIG. 3k, only the durations of open-loop bursts are adjusted. The durations of closed-loop pulses are not scaled to meet any particular on-to-off-time ratio.

In the example of FIG. 3m, durations of both closed-loop and open-loop bursts are adjusted to compensate for reduced battery life associated with application of a responsive, closed-loop burst. FIG. 3l shows a dosing pattern including only programmed, open-loop bursts 420, 422 and 424. Each burst lasts for 4 seconds and is preceded by an off-time that lasts for 20 seconds. Thus, an off-time begins at t=0 and lasts until t=20, at which time an open-loop burst 420 begins and lasts until t=24. At t=24, the next off-time begins, and so forth. By alternating 4 second on-cycles with 20 second off-times, an on-time to off-time ratio of 1:5 is achieved and maintained.

FIG. 3m shows a pattern similar to that shown in FIG. 3l except it includes an unscheduled, closed-loop burst 432. The duration (i.e., on-time) of closed-loop burst 432 is not full-length (i.e., 4-seconds), however. Instead, the duration of closed-loop burst 432 is adjusted depending on the duration of the off-time that precedes it, much like that of burst 414 in FIG. 3k. Because the duration of the off-time between bursts 430 and 432 is 10 seconds, and because the desired ratio of on-time to off-time is 1:5, burst 432 is 2 seconds long, followed by an off-time of 10 seconds that lasts until the next scheduled, open-loop burst 434 is applied. Again, although burst 434 is delivered as programmed, the duration of burst 434 depends on the duration of the off-time that precedes it. The duration of the off-time preceding the burst 434 is 10 seconds, so the burst 434 is 2 seconds long, thus maintaining the desired 1:5 ratio. The next off-time is 20 seconds long and is followed by the regularly scheduled burst 436, which is a full 4 seconds in duration.

As previously explained, responsive, closed-loop bursts are delivered as a result of detecting some event. In at least some cases, this event is the detection of an impending or already-occurring seizure (e.g., detected by measuring one or more cardiac parameters). Although such an event detection is used to trigger the delivery of a closed-loop burst, the timing of such an event detection also may be used to adjust the regularly scheduled open-loop dosing. For instance, if seizures tend to occur within some threshold amount of time from the ends of off-time periods but before the next scheduled burst, the off-times' duration may be reduced, thereby causing the open-loop cycles to be delivered more frequently. In another example, if seizures tend to occur within some threshold amount of time after a stimulation burst, it may be the case that the stimulation parameters are counterproductive to at least some seizure events. Thus, stimulation parameters (e.g., frequency of the electrical pulses comprising a burst) may be adjusted so that seizures become less frequent. In other embodiments, stimulation may be suspended, reduced or discontinued altogether.

In embodiments involving closed-loop stimulation, an event (such as detection of an epileptic seizure) may be based upon an algorithm that processes a body parameter such as heart rate. Depending upon the algorithm and its triggering thresholds, event detection parameters may be undesirably stringent, and may result in undesirably low amounts of stimulation. Similarly, event detection parameters may sometimes be undesirably lax, resulting in undesirably high amounts of stimulation. Accordingly, in at least some embodiments, the IMD 110 may be programmed to include minimum and maximum stimulation constraints. The IMD 110 may compare the actual amount of stimulation (i.e. electrical charge) applied to the target tissue (based, for example, on the percentage of real time that stimulation is applied, or the amount of charge delivered to the nerve within one or more time frames, or the amount of time at which stimulation above a particular frequency is applied to the nerve) to these minimum and maximum constraints to ensure that the IMD 110 is not under-stimulating or over-stimulating the patient. In case the actual amount of stimulation falls below the minimum stimulation constraint, the event detection (i.e., algorithm) parameters may be modified (i.e., lowered) so that the actual amount of stimulation (in this case, rate of charge delivery) increases to meet or exceed the minimum stimulation constraint. Similarly, in case the actual stimulation amount exceeds the maximum stimulation constraint, the event detection parameters may be modified (i.e., increased) so that the actual amount of stimulation decreases to meet or fall below the maximum stimulation constraint. In this way, the actual amount of stimulation (on a charge and/or time basis) may be dynamically regulated into a desired and/or programmed range.

The techniques described herein may be implemented in various combinations. For example, the technique for reducing burst duration (depicted above in FIG. 3i) may be combined with the technique for increasing off-time duration (illustrated in FIG. 3g). This combination, in turn, may be combined with one or more additional techniques. Any and all combinations of the techniques described herein are included within the scope of this disclosure.

At a more general level, additional techniques to compensate for reduced battery life associated with responsive, closed-loop bursts are possible when the full array of programmable parameters that define electrical stimulation therapies are considered. In the embodiment of FIG. 3c, programmed pulse bursts are adjusted by resynchronizing the programmed off-time to be measured from an unplanned, closed-loop burst rather than from the previously delivered open-loop burst. In the embodiment of FIG. 3d, the off-time following a closed-loop burst is increased to cause the closed-loop burst to be considered as a substitute for the open-loop burst that would have been delivered next. FIGS. 3f and 3g depict inserting additional off-time between one or more of open-loop bursts following a closed-loop burst to recover the early intervention time (EIT) associated with the closed-loop burst. FIGS. 3i and 3k depict reducing the on-times of one or more open-loop bursts following a closed-loop burst to recover the additional charge (CLC) applied to the target tissue in the closed-loop burst. In FIG. 3m, the on-time of both the closed-loop and the next following open-loop burst are determined based upon their respective timing relative to the previous open-loop burst (in the case of the closed-loop burst) and the time of delivery of the closed-loop burst (in the case of the next open-loop burst), with the goal of maintaining a predetermined rate of electrical charge delivery to the target tissue.

In addition to adjusting off-time and on-time, frequency and pulse-width may also be adjusted to compensate for the CLC delivered in an unprogrammed, closed-loop burst. For example, the pulse width for some or all of the pulses of one or more open-loop bursts that follow an unprogrammed, closed-loop burst may be reduced to recover the CLC delivered in the closed-loop burst. For example, although not depicted in the Figures, the programmed pulse width of an open-loop stimulation program for a patient may be set at 250 microseconds. Following delivery of a closed-loop burst having the same on-time, frequency, pulse width, and current settings as an open-loop burst, the pulse width of the next 5 subsequent open-loop bursts may be reduced to 200 microseconds to recover the CLC applied in the closed-loop burst. Similarly, where open-loop frequency is programmed at 30 Hz, the frequency of the next 3 open-loop bursts may be reduced to 20 Hz to recover the CLC applied during a closed-loop burst (assuming that the closed-loop burst has the same one-time, frequency, pulse width and current as a programmed open-loop burst). Finally, when open-loop bursts have a programmed current of 2 milliamperes (mA), the charge delivered in a closed-loop burst having the same program parameters as the open-loop bursts may be recovered by reducing the programmed current to 1 mA for the next two open-loop bursts following the closed-loop burst. It will also be appreciated that slightly different adjustments to on-time, off-time, frequency, pulse width and/or current may be made to recover the charged applied in a closed-loop burst having different parameters (for example, a different on-time, frequency, pulse width, and/or current) than a programmed open-loop burst.

More generally, following delivery of a responsive, closed-loop burst, one of more of the off-time, on-time, pulse width and current for one or more subsequent open loop bursts may be adjusted to maintain the same rate of electrical charge delivery (i.e., coulombs of charge per unit time) as provided in programmed, open loop stimulation with no closed-loop stimulation. In other embodiments, one or more of the on-time, pulse width, and current of the closed-loop burst may also be adjusted based upon the time following the previous programmed, open-loop burst that the closed-loop burst is initiated.

Figure 4:
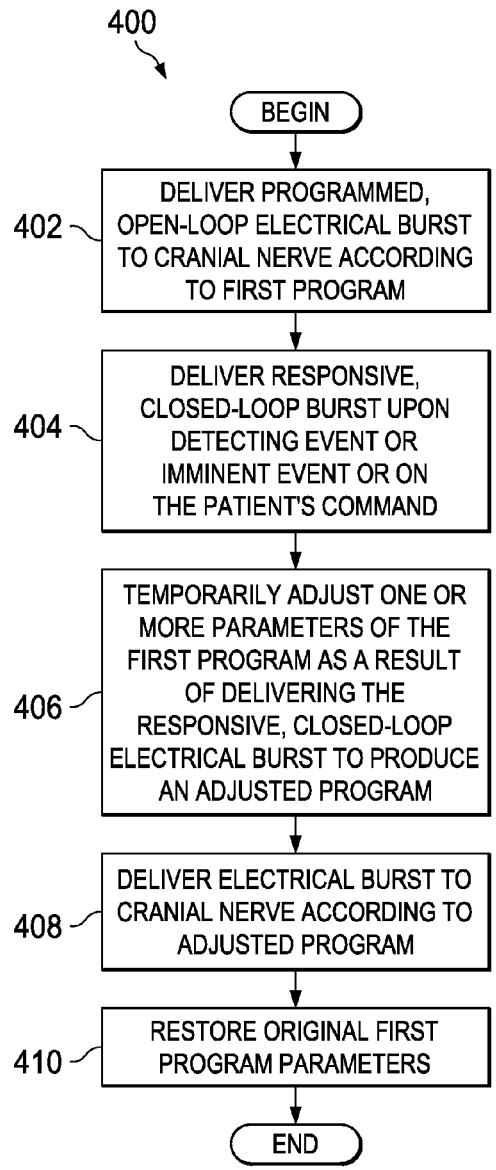
FIG. 4 shows a flow diagram of an illustrative method usable in conjunction with the system of FIG. 1, consistent with embodiments of the invention.

The foregoing techniques may be generally described by way of method 400 of FIG. 4. The method 400 begins by delivering one or more programmed, open-loop electrical bursts to a cranial nerve according to a first program (block 402). The cranial nerve, in at least some embodiments, is the vagus nerve. The first program preferably is defined by a plurality of parameters programmed into the IMD 110, the external device 150, or some combination thereof. The method 400 further comprises delivering a responsive, closed-loop electrical burst upon detecting an event or imminent event (e.g., a seizure) or on a user's manual command (block 404). The method 400 further comprises temporarily adjusting at least one parameter defining the first program as a result of delivering the responsive, closed-loop electrical burst, thereby producing an adjusted program (block 406), where the adjusted program is characterized by restoring at least some portion of the battery life lost as a result of the delivery of the closed-loop burst. The adjusted program, like the first program, may be programmed in whole or part into the IMD 110, the external device 150, or some combination thereof. The program adjustment may employ any or all of the various techniques described herein and also may employ techniques not explicitly described herein. The method 400 still further comprises delivering an electrical pulse or pulses to the cranial nerve according to the adjusted schedule (block 408), and restoring the original program parameters of the first program (block 410).

As previously explained herein, techniques for conserving battery life are described first, followed by a description of techniques for accurately predicting battery life. The techniques for conserving battery life having been fully described, the techniques for accurately predicting battery life now follow.

Generally, in at least some battery life prediction embodiments, an estimate of battery longevity is first made based on both an open-loop stimulation program and predicted closed-loop stimulation (based on the patient's personal disease history, detector performance capabilities, and/or one or more of a variety of other factors). Subsequently, in such embodiments, the rate of closed-loop stimulation that is actually provided by the IMD 110 when the IMD 110 is implanted and operating inside the patient's body (i.e., the rate of closed-loop stimulation "in real life") is recorded and is used to adjust the estimate of battery longevity. Alternatively to the determination in step 504 of the rate at which closed-loop electrical stimulation bursts are actually applied to a cranial nerve, the IMD 110 may be programmed to deliver only open-loop therapy, but to record when closed-loop therapy would have been delivered had closed-loop therapy been enabled. This recorded information can then be used to estimate battery longevity. The estimation may be used to adjust IMD parameters in consideration of estimated battery longevity and, if desired, closed-loop stimulation may thereafter be enabled.

In some embodiments, longevity estimates of the IMD 110 (more specifically, longevity of the power source 210) may be determined by first estimating longevity based on (1) programmed, open-loop stimulation and (2) estimates of responsive, closed-loop stimulation using the patient's personal disease history and the detection capabilities (e.g., sensitivity) of the detection logic 270. After longevity of the IMD 110 is estimated in this way, the estimate is refined by monitoring the quantity of responsive, closed-loop stimulation bursts that are delivered by the IMD 110 after the IMD 110 is implanted in the patient's body. A log of such stimulation activity may be recorded in storage 280 and later provided to the external unit 150 via the communication unit 260. Alternatively, the log may be provided in real-time to the external unit 150 via the communication unit 260. In either case, the actual closed-loop stimulation data is used to refine the initial estimate regarding longevity of the IMD 110.

In some embodiments, a different technique may be used to refine the initial estimate regarding longevity of the IMD 110. In such embodiments, the IMD 110 is programmed to deliver not only scheduled, open-loop stimulations but is further programmed to record each instance at which the IMD 110 would have delivered an unscheduled, closed-loop stimulation had it been enabled to do so. These recorded data may be provided to the external unit 150 in real-time or may be stored in storage 280 for subsequent transfer to the external unit 150. In either case, the recorded data then are used to refine the initial estimate regarding longevity of the IMD 110.

Initial estimates and refinements thereto preferably are performed by the external unit 150 but also may be performed by the IMD 110 (e.g., by the power-source controller 220, the power regulation unit 240, stimulation logic 255 or any other suitable circuit logic). In some cases, portions of the initial estimates and/or refinements may be performed on the IMD 110 with the remainder of the estimates and/or refinements performed on the external unit 150. Both the initial estimates and refined predictions are displayed or otherwise provided to an end-user of the external unit 150 (e.g., the patient's physician). The end-user may adjust IMD 110 closed-loop algorithm parameters (e.g., maximum and minimum stimulation thresholds at which a signal to initiate closed-loop stimulation is generated) in light of the estimated longevity. The end-user also may enable or disable responsive, closed-loop stimulations by the IMD 110.

Figure 5:
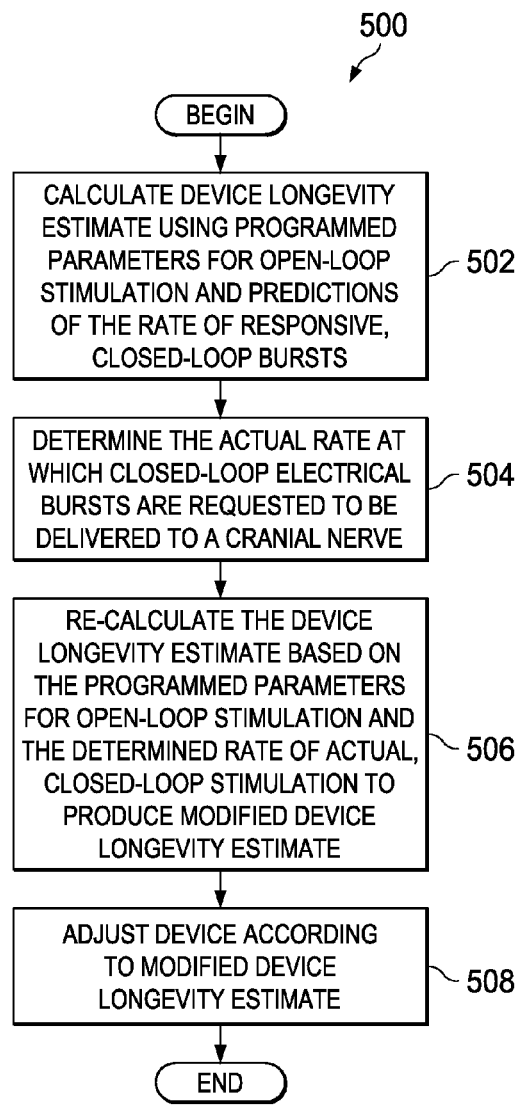
FIG. 5 shows a flow diagram of another illustrative method usable in conjunction with the system of FIG. 1, consistent with embodiments of the invention.

FIG. 5 shows a flow diagram of a method 500 in accordance with embodiments. The method 500 begins by calculating an IMD longevity estimate using program parameters for open-loop electrical stimulation and predictions of the rate of responsive, closed-loop electrical stimulation (block 502). The method 500 also comprises determining the actual rate at which closed-loop electrical bursts are requested to be delivered to a cranial nerve (e.g., the vagus nerve) (block 504). The action of block 504 may occur in multiple ways. For example, in some embodiments, the action of block 504 may include refining the initial calculation of block 502 based on actual closed-loop stimulation bursts that are delivered to the cranial nerve. In some embodiments, closed-loop stimulation is not implemented, and the rate of detection of events that would have triggered closed-loop stimulation had it been enabled are used instead of actual closed-loop stimulation The method 500 further comprises re-calculating the device longevity estimate based on the program parameters for open-loop stimulation and the determination of block 504 to produce a modified device longevity estimate (block 506). The method 500 may, in some embodiments, further comprise modifying the operation of the device based on the modified device longevity calculation (block 508). In the action of block 508, the refined predictions may be provided to the end-user (e.g., a physician) so that the user may take appropriate action by modifying the operation of the IMD 110 as described above. For instance, IMD 110 parameters (e.g., maximum and minimum stimulation thresholds) may be adjusted, and closed-loop stimulation may be activated or deactivated.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A method comprising:

applying an electrical signal of electrical signals of scheduled stimulation to a neural structure via an implantable medical device (IMD), wherein the scheduled stimulation is defined by a plurality of parameters and characterized by a first rate of electrical charge delivery to the neural structure, and wherein the first rate is based on one or more of the plurality of parameters;

detecting an event at the IMD after application of the electrical signal and before application of a next scheduled electrical signal of the scheduled stimulation;

applying event stimulation to the neural structure via the IMD in response to detection of the event;

adjusting at least one parameter of the plurality of parameters that define the scheduled stimulation in response to detection of the event to define adjusted stimulation characterized by a second rate of electrical charge delivery to the neural structure that is less than the first rate;

applying the adjusted stimulation to the neural structure via the IMD after application of the event stimulation to compensate for electrical charge delivery due to the event stimulation; and applying at least one electrical signal of the scheduled stimulation to the neural structure via the IMD after application of the adjusted stimulation.

2. The method of claim 1, wherein the scheduled stimulation comprises a plurality of pulse bursts separated by an off-time period, and wherein applying the adjusted stimulation to the neural structure comprises skipping at least one pulse burst of the scheduled stimulation after the application of the event stimulation.

3. The method of claim 1, further comprising determining an intervention time associated with the application of the event stimulation, wherein the scheduled stimulation comprises a plurality of pulse bursts separated by a first off-time period, wherein the adjusted stimulation comprises at least one pulse burst followed by a second off-time period, wherein the intervention time is a difference between the first off-time period and an actual off-time elapsed from application of the electrical signal to the application of the event stimulation, and wherein the second off-time period is determined by adding at least a portion of the intervention time to the first off-time period.

4. The method of claim 1, wherein the scheduled stimulation comprises a plurality of electrical pulse bursts, wherein each pulse burst has a duration defined by a first on-time, wherein each pulse burst is separated from an adjacent pulse burst by a first off-time, wherein applying the adjusted stimulation to the neural structure comprises delivering n pulse bursts after application of the event stimulation, and wherein the n pulse bursts are defined by a second on-time that is shorter than the first on-time.

5. The method of claim 1, wherein the scheduled stimulation comprises a plurality of pulse bursts, wherein each pulse burst has a duration defined by a first on-time, wherein each pulse burst is separated from an adjacent pulse burst by a first off-time, wherein the adjusted stimulation comprises at least one pulse burst having a second on-time followed by a second off-time, wherein applying the event stimulation comprises generating an event electrical signal having a duration defined by a fraction of the first off-time; and wherein the second on-time is defined by a second fraction of the first off-time.

6. A system, comprising:

detection logic adapted to detect an event; and stimulation logic coupled to the detection logic and adapted to apply scheduled stimulation, adjusted stimulation, and event stimulation to a neural structure;

wherein the scheduled stimulation is characterized by a plurality of parameters and by a first rate of electrical charge delivery to the neural structure that is based on the plurality of parameters;

wherein, upon receipt of notification from the detection logic of detection of the event after application of an electrical signal of the scheduled stimulation and before application of a next scheduled electrical signal of the scheduled stimulation, the stimulation logic applies event stimulation to the neural structure;

wherein, upon application of the event stimulation to the neural structure, the stimulation logic adjusts one or more parameters of the plurality of parameters to define the adjusted stimulation, wherein the adjusted stimulation is characterized by a second rate of electrical charge delivery to the neural structure that is less than the first rate; and wherein application of the adjusted stimulation to the neural structure compensates for electrical charge delivery due to the event stimulation.

7. The system of claim 6, wherein the stimulation logic is adapted to apply one or more electrical signals of the scheduled stimulation to the neural structure after application of the adjusted stimulation to the neural structure.

8. The system of claim 7, wherein the scheduled stimulation comprises a plurality of pulse bursts, wherein each pulse burst has a duration defined by a first on-time, wherein each pulse burst is separated from an adjacent pulse burst by a first programmed off-time, and wherein the adjusted stimulation comprises the first off-time, and wherein the scheduled stimulation, starting with a pulse burst, resumes after the first off-time of the adjusted stimulation.

9. The system of claim 6, wherein the scheduled stimulation comprises a plurality of pulse bursts, wherein each pulse burst has a duration defined by a first on-time, wherein each pulse burst is separated from an adjacent pulse burst by a first off-time, and wherein the stimulation logic skips a next pulse burst of the scheduled stimulation after the application of the event stimulation.

10. The system of claim 6, wherein the scheduled stimulation comprises a plurality of pulse bursts separated by a first off-time period, wherein the adjusted stimulation comprises at least one pulse burst followed by a second off-time period, wherein the stimulation logic determines an intervention time associated with the application of the event stimulation, wherein the intervention time is a difference between the first off-time period and an actual off-time elapsed from application of the electrical signal to the application of the event stimulation, and wherein a least a portion of the intervention time is added to the firstoff-time period to determine the second off-time period.

11. The system of claim 6, wherein the scheduled stimulation comprises a plurality of pulse bursts, wherein each pulse burst has a duration defined by a first on-time, wherein each pulse burst is separated from an adjacent pulse burst by a first off-time, wherein the stimulation logic delivers n pulse bursts after application of the event stimulation, and wherein the n pulse bursts are defined by a second on-time that is shorter than the first on-time.

12. The system of claim 6, wherein the scheduled stimulation comprises a plurality of pulse bursts, wherein each pulse burst has a duration defined by a first on-time, wherein each pulse burst is separated from an adjacent pulse burst by a first off-time, wherein the adjusted stimulation comprises at least one pulse burst having a second on-time followed by a second off-time, wherein the stimulation logic generates the event stimulation having a duration defined by a fraction of the first off-time, and wherein the second on-time is defined by a second fraction of the first off-time.

13. A non-transitory computer-readable medium comprising instructions executable by a processor to:
- cause an electrical signal of electrical signals of scheduled stimulation to be sent to an electrode assembly, wherein the scheduled stimulation is characterized by a first charge delivery rate;
- cause event stimulation to be sent to the electrode assembly in response to detection of an event after the electrical signal is sent and before a next scheduled electrical signal of the scheduled stimulation is to be sent;
- determine adjusted stimulation characterized by a second electrical charge delivery rate that is less than the first charge delivery rate to compensate for electrical charge delivery due to the event stimulation sent to the electrode assembly; and
- cause the adjusted stimulation to be sent to the electrode assembly.

14. The non-transitory computer-readable medium of claim 13, further comprising instructions executable by the processor to resume delivery of the scheduled stimulation to the electrode assembly after the adjusted stimulation is sent to the electrode assembly.

15. The non-transitory computer-readable medium of claim 13, wherein the scheduled stimulation comprises a plurality of pulse bursts, wherein each pulse burst has a duration defined by a first on-time, wherein each pulse burst is separated from an adjacent pulse burst by a first off-time, wherein the event stimulation comprises a pulse burst with a duration of the first on-time that begins a first time after an end of the electrical signal, and wherein the adjusted stimulation has a second off-time followed by a pulse burst with a duration of the first on-time, wherein the second off-time equals the first off-time plus a difference between the first off-time and the first on-time.

16. The non-transitory computer-readable medium of claim 13, wherein the scheduled stimulation comprises a plurality of pulse bursts, wherein each pulse burst has a duration defined by a first on-time, wherein each pulse burst is separated from an adjacent pulse burst by a first off-time, and wherein the instructions executable by the processor to determine the adjusted stimulation comprise instructions executable by the processor to:
- determine a time difference between an end of a pulse burst of the electrical signal and a start of a pulse burst of the event stimulation;
- schedule a first pulse burst of the adjusted stimulation to begin after the first off-time elapses from an end of the pulse burst of the event stimulation; and
- schedule one or more additional pulse bursts of the adjusted stimulation, wherein the one or more additional pulse bursts are to begin after an elapse time from a most recent pulse burst, wherein the elapse time equals the first off-time plus the time difference divided by a number of the one or more additional pulse bursts.

17. The non-transitory computer-readable medium of claim 13, wherein the scheduled stimulation comprises a plurality of pulse bursts, wherein each pulse burst has a duration defined by a first on-time, wherein the event stimulation comprises a pulse burst with a duration of the first on-time, wherein the adjusted stimulation comprises one or more second pulse bursts, and wherein a duration of at least one second pulse burst is less than the first on-time.

18. The non-transitory computer-readable medium of claim 13, wherein the scheduled stimulation comprises a plurality of pulse bursts, wherein each pulse burst has a duration defined by a first on-time, wherein the event stimulation comprises a pulse burst with a duration that is less than the first on-time, and wherein the adjusted stimulation comprises one or more second pulse bursts, and wherein a duration of at least one second pulse burst is less than the first on-time.

19. The non-transitory computer-readable medium of claim 13, wherein detection of the event comprises receipt of manual activation of signal delivery.

20. The non-transitory computer-readable medium of claim 13, wherein the instructions executable by the processor further comprise instructions executable by the processor to make a determination that at least one detected body parameter is outside of an acceptable range for the least one body parameter to detect the event.

* * * * *